US012744776B2

(12) United States Patent
Gamble et al.

(10) Patent No.: US 12,744,776 B2
(45) Date of Patent: Sep. 22, 2026

(54) AUTHENTICATION OF MEDICAL DEVICES

(71) Applicant: Welch Allyn, Inc., Skaneateles Falls, NY (US)

(72) Inventors: David D. Gamble, East Syracuse, NY (US); Douglas Fenster, Onondaga Hill, NY (US); Adam Webster, Painted Post, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 187 days.

(21) Appl. No.: 18/469,220

(22) Filed: Sep. 18, 2023

(65) Prior Publication Data

US 2024/0114027 A1 Apr. 4, 2024

Related U.S. Application Data

(60) Provisional application No. 63/377,576, filed on Sep. 29, 2022.

(51) Int. Cl.
*H04L 9/40* (2022.01)
*G16H 40/67* (2018.01)

(52) U.S. Cl.
CPC ......... *H04L 63/0876* (2013.01); *G16H 40/67* (2018.01)

(58) Field of Classification Search
None
See application file for complete search history.

(56) References Cited

U.S. PATENT DOCUMENTS 10,285,589 B2 5/2019 Hart et al.
10,772,495 B2 9/2020 Farchione et al.
10,993,613 B2 5/2021 Hart et al.
11,138,732 B2 10/2021 Hart et al.
2007/0226785 A1* 9/2007 Chow .................. H04L 9/3271 726/8
2018/0020918 A1* 1/2018 Redei ..................... G16H 40/67 600/300
2020/0036723 A1* 1/2020 Ranchod .................. G06F 8/60
2020/0405148 A1 12/2020 Tran
2021/0250344 A1 8/2021 Qi et al.
2022/0039653 A1 2/2022 Meyerson et al.
2023/0016417 A1 1/2023 Hart
(Continued)

FOREIGN PATENT DOCUMENTS

EP 3 113 513 A1 1/2017
KR 10-1837848 B1 3/2018

OTHER PUBLICATIONS

International Search Report and Written Opinion for Application No. PCT/US2023/033038 mailed Dec. 18, 2023.

*Primary Examiner* — Philip J Chea
*Assistant Examiner* — James Ross Hollister
(74) *Attorney, Agent, or Firm* — Merchant & Gould P.C.

(57) ABSTRACT

A system for authenticating a medical device is described. The system receives a request from a medical device to access operations or data of an external service provider. The system determines whether the request received from the medical device is valid. When the request is valid, the system generates a token that is customized based on the external service provider identified in the request, and the system transfers the token to medical device, the token enabling the medical device to access the operations or data of the external service provider.

12 Claims, 8 Drawing Sheets

(56) References Cited

U.S. PATENT DOCUMENTS

| | | | | |
|---|---|---|---|---|
| 2023/0224293 | A1* | 7/2023 | Rohlwing | H04L 63/0823 713/156 |
| 2024/0080195 | A1* | 3/2024 | Schrum | G06F 21/62 |
| 2024/0296950 | A1* | 9/2024 | Stotts | G16H 40/67 |
| 2025/0098958 | A1* | 3/2025 | Dirghangi | G16H 10/60 |

* cited by examiner

AUTHENTICATION OF MEDICAL DEVICES

BACKGROUND

Diabetic retinopathy and other eye diseases can be diagnosed by studying an image of the retina. Retinal images can be reviewed manually by a clinician. However, manual review is labor-intensive process and subject to human error. In some instances, an overread service is used to provide additional resources for analyzing retinal images.

SUMMARY

In general terms, the present disclosure relates to authenticating a medical device for access to operations or data of an external service provider. Various aspects are described in this disclosure, which include, but are not limited to, the following aspects.

One aspect relates to a system for authenticating a medical device, the system comprising: at least one processing device; and a memory device storing instructions which, when executed by the at least one processing device, cause the at least one processing device to: receive a request from a medical device to access operations or data of an external service provider; determine whether the request received from the medical device is valid; when the request is valid, generate a token that is customized based on the external service provider identified in the request; and transfer the token to medical device, the token enabling the medical device to access the operations or data of the external service provider.

Another aspect relates to a method for authenticating a medical device, the method comprising: receiving a request from a medical device to access operations or data of an external service provider; determining whether the request received from the medical device is valid; when the request is valid, generating a token that is customized based on the external service provider identified in the request; and transferring the token to medical device, the token enabling the medical device to access the operations or data of the external service provider.

Another aspect relates to a non-transitory computer-readable data storage medium comprising instructions that, when executed, cause at least one computing device to: receive a request from a medical device to access operations or data of an external service provider; determine whether the request received from the medical device is valid; when the request is valid, generate a token that is customized based on the external service provider identified in the request; and transfer the token to medical device, the token enabling the medical device to access the operations or data of the external service provider.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
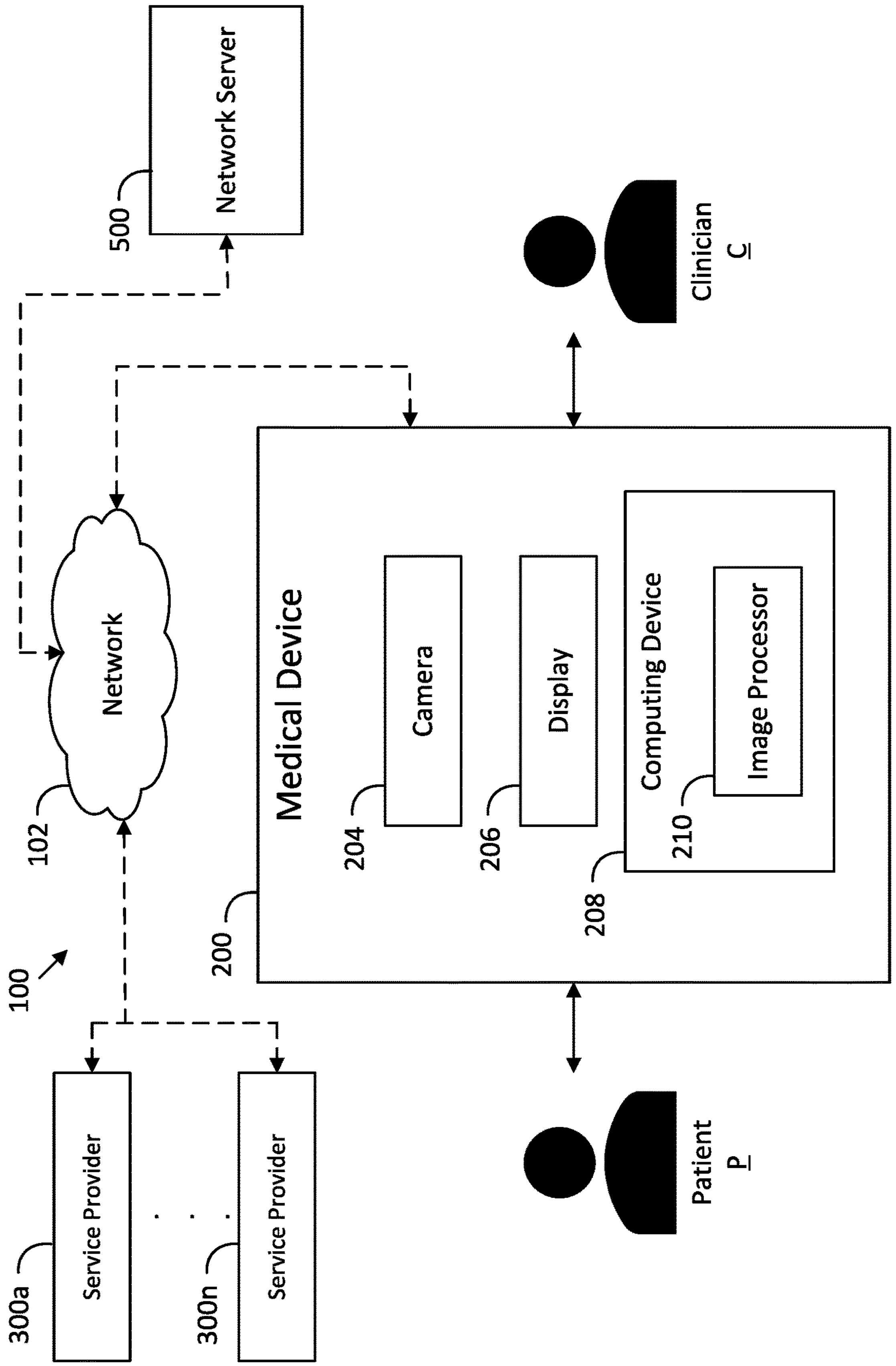
FIG. 1 schematically illustrates an example of a system for capturing and analyzing diagnostic data, the system including a medical device connected to a network server.

FIG. 1 schematically illustrates an example of a system 100 for capturing and analyzing diagnostic data. The system 100 includes a medical device 200 connected to a network 102. The medical device 200 is operable by a clinician C to capture the diagnostic data from a patient P, and to transmit the diagnostic data to one or more external service providers 300*a*-300*n* for analysis. The one or more external service providers 300*a*-300*n* return an analysis and/or a clinical report based on the captured diagnostic data to the medical device 200. In some examples, the one or more external service providers 300*a*-300*n* provide overread services for analyzing the diagnostic data captured by the medical device 200.

In the example illustrated in FIG. 1, the medical device 200 is an eye imager that the clinician C uses to capture one or more fundus images of the patient P's eyes to screen, monitor, and/or diagnose one or more eye diseases such as diabetic retinopathy, macular degeneration, glaucoma, and papilledema. As used herein, "fundus" refers to the eye fundus and includes the retina, optic disc, macula, fovea, retinal blood vessels, and other anatomical structures of the eye.

The clinician C can use the medical device 200 to transmit the fundus images to the external service providers 300*a*-300*n* via the network 102, and to receive an analysis and/or a diagnostic report based on the fundus images from the one or more external service providers 300*a*-300*n* via the network 102. In some instances, the clinician C who operates the medical device 200 is different from the clinician who evaluates the fundus images captured by the medical device 200. In some examples, at least some of the external service providers 300*a*-300*n* perform artificial intelligence and machine learning techniques to analyze the fundus images captured by the medical device 200 for eye disease screening, monitoring, and/or diagnosis.

In alternative examples, the system 100 can include various types of medical and/or diagnostic devices connected to the external service provider 300 via the network 102 such as including, without limitation, otoscopes, ophthalmoscopes, dermatoscopes, electrocardiogram (EKG) machines, and the like. Accordingly, the disclosure provided herein is not necessarily limited to fundus imagers, and may also be applies to other diagnostic medical devices.

The medical device 200 further includes a computing device 208 in communication with a camera 204 and a display 206. The computing device 208 includes an image processor 210 that processes the images captured by the camera 204 for display on the display 206.

The medical device 200 is operated by the clinician C to create a set of digital images of the patient P's eye fundus. As an example, the fundus images created by the medical device 200 can be used to screen for an eye disease such as diabetic retinopathy. As a further example, the fundus images created by the medical device 200 can be used to diagnose a disease such as diabetic retinopathy or monitor the progression of a disease such as diabetic retinopathy.

One technique for fundus imaging requires mydriasis, or the dilation of the patient P's pupil, which can be painful and/or inconvenient to the patient P. The medical device 200 does not require a mydriatic drug to be administered to the patient P before imaging. However, the medical device 200 can image the fundus when a mydriatic drug has been administered.

The camera 204 is communicatively connected to the image processor 210. In this example, the camera 204 is a digital camera that can include a lens, an aperture, and a sensor array. In some examples, the camera 204 lens is a variable focus lens, such as a lens moved by a step motor, or a fluid lens, also known as a liquid lens in the art. The camera 204 is configured to record images of the fundus one eye at a time. In other examples, the camera 204 is configured to record an image of both eyes substantially simultaneously. In such examples, the medical device 200 can include two separate cameras, each capturing a fundus image of an eye of the patient P.

In this example, the image processor 210 is communicatively coupled to the camera 204 and is configured to communicate with the display 206. The display 206 functions to reproduce the images created by the camera 204 in a size and format readable by the clinician C. For example, the display 206 can include a liquid crystal display (LCD) and/or active matrix organic light emitting diode (AMOLED) display. In some examples, the display 206 includes a touchscreen that operates as an input device for medical device 200.

The network 102 may include any type of wireless network, wired network, or any combination of wireless and wired networks. Wireless connections can include broadband cellular network connections (e.g., 4G and 5G) and connections made using protocols such as 802.11a, b, and/or g. In some examples, wireless connections can be accomplished using one or more wireless protocols, such as Bluetooth, Wi-Fi, radio-frequency identification (RFID), Zigbee. In some examples, wired connections can be accomplished through Ethernet. In some examples, the network 102 includes the Internet. Other configurations are possible.

As further shown in FIG. 1, a network server 500 is communicatively connected to the medical device 200 via the network 102. The network server 500 can include aspects of a wireless client-server that is a front-end interface with which the clinician C operating the medical device 200 interacts with. Also, the network server 500 can include aspects of an authorization server that is a backend unit managing the task of verifying the credentials of the medical device 200, generating authentication tokens, and sending the authentication tokens to the medical device 200 allowing the medical device to access an external service provider 300, which is an example of a resource server. The external service providers 300 is an entry point where the medical device 200 enters the authentication token generated by the network server 500 to gain access to the operations and/or data of the external service provider.

Figure 2:
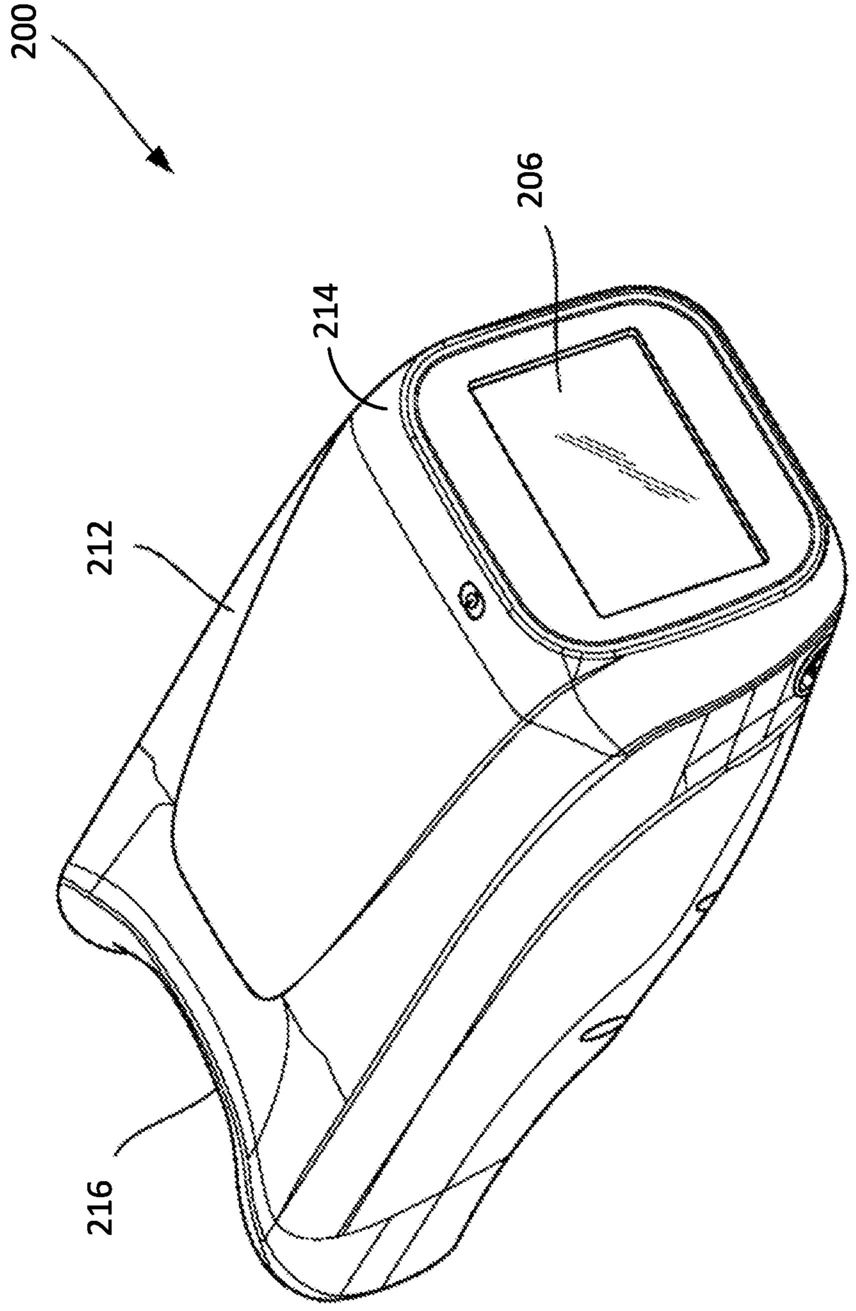
FIG. 2 illustrates an isometric view of an example of the medical device in the system of FIG. 1, the medical device being shown from a clinician perspective.
Figure 3:
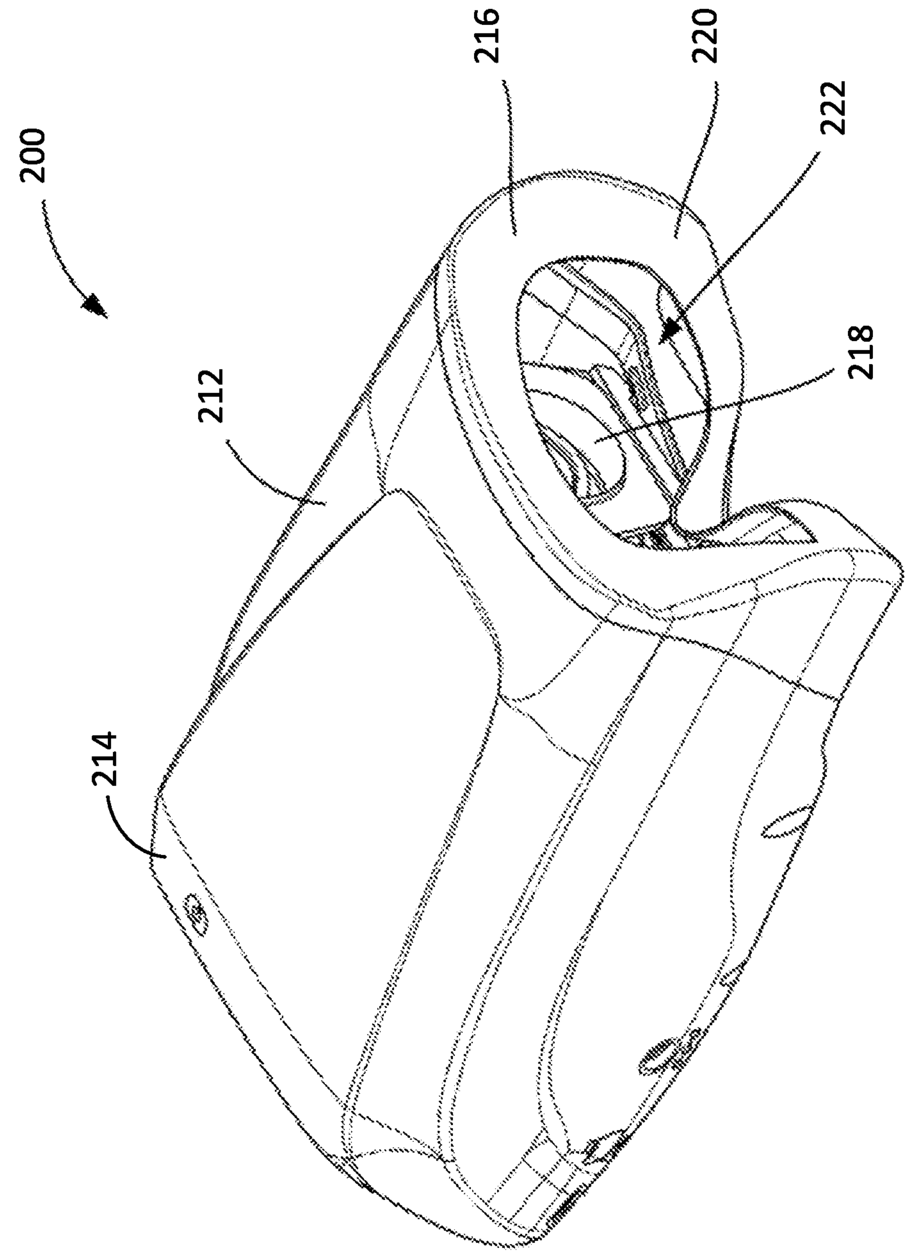
FIG. 3 illustrates another isometric view of the medical device of FIG. 2, the medical device being shown from a patient perspective.
Figure 4:
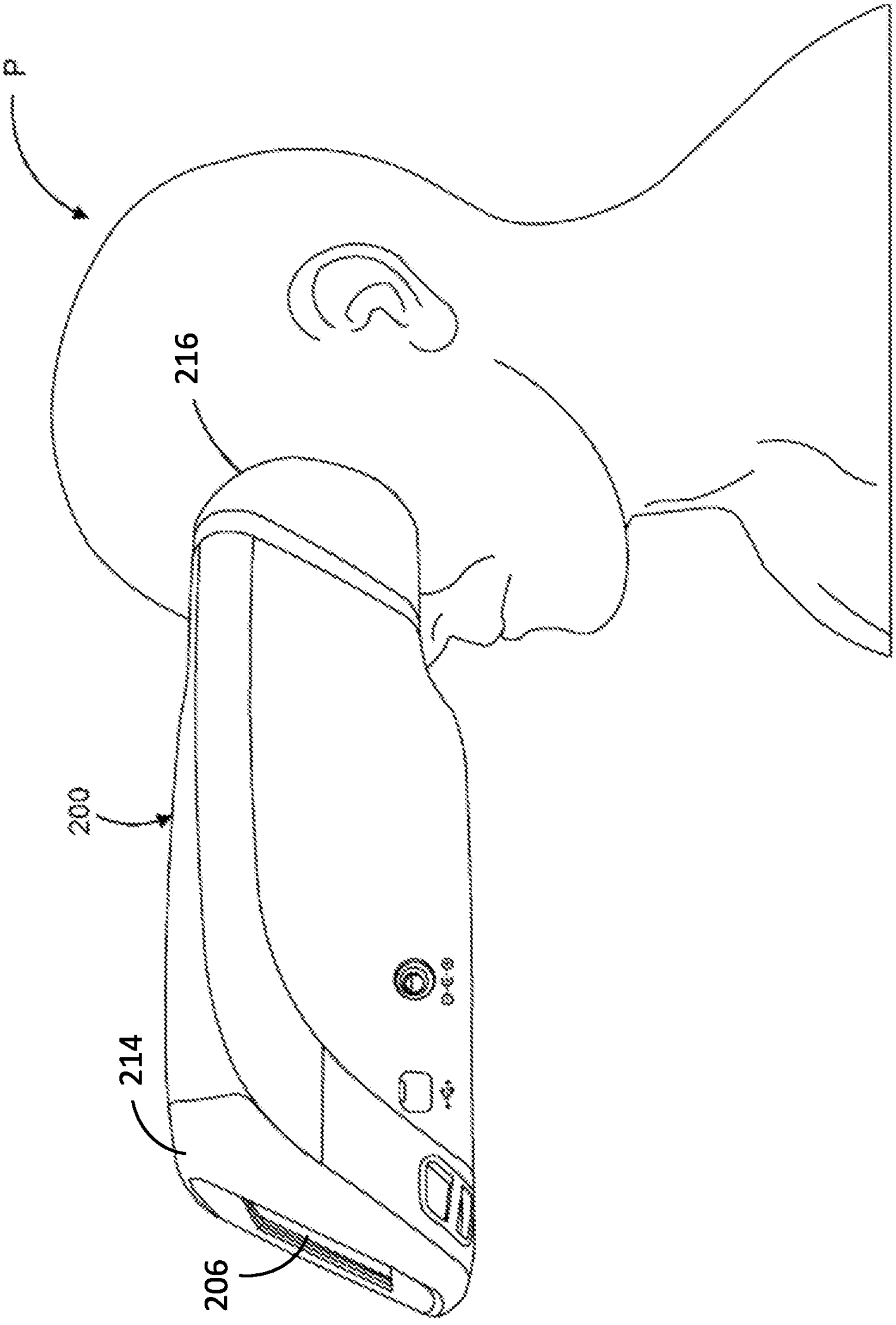
FIG. 4 illustrates the medical device of FIG. 2 positioned against a patient's head.

FIG. 2 illustrates an isometric view of an example of the medical device 200 from a perspective of the clinician C. FIG. 3 illustrates an isometric view of the medical device 200 from a perspective of the patient P. FIG. 4 illustrates the medical device 200 positioned against the patient P's head. Referring now to FIGS. 1-4, the medical device 200 includes a housing 212 that is sized and shaped for handheld use. The housing 212 extends from a first end 214 that faces the clinician C during use to a second end 216 that faces the patient P during use.

As shown in FIG. 2, the housing 212 supports the display 206 at the first end 214. In examples where the display 206 includes a touchscreen, the display 206 can display controls for operating the camera 204 to capture fundus images. Once the fundus images have been captured by the camera 204, and the display 206 can display the fundus images for viewing by the clinician C. The housing 212 can additionally support one or more user input buttons at the first end 214. The medical device 200 enables the clinician C to implement one or more automatic and/or manual workflows for the capture of fundus images of the patient P's eyes.

In alternative examples, the display 206 is provided on a device separate from the medical device 200. For example, the display 206 can be provided on a smartphone, a tablet computer, or other external monitor that can communicate with the medical device 200 such as through the network 102, and/or through another type of network.

As shown in FIGS. 3 and 4, the housing 212 at the second end 216 is sized and shaped to engage one or both eyes of the patient P. The second end 216 of the housing 212 includes a surface 220 for engaging the patient P's head. For example, the surface 220 is configured to be positioned against the patient P's face and to surround both eyes of the patient P. The camera 204 is positioned within a cavity 222 formed inside the housing 212.

As further shown in FIG. 3, the housing 212 at the second end 216 includes one or two apertures 218 for imaging one or both eyes of the patient at a time. In some examples, a positional guide such as an adjustable chin rest can be used to help align the patient's P eyes with the one or two apertures 218. In some examples, the housing 212 supports means for raising and lowering the camera 204 for alignment with the patient P's eyes. In some examples, the camera 204 can move in three directions to image the fundus of both eyes of the patient P while the housing 212 is held positioned against the patient P's head, as shown in FIG. 4.

As shown in FIG. 4, once the patient P's eyes are aligned, the clinician C can initiate an image capture sequence on the medical device 200. In examples where the display 206 includes a touchscreen, the clinician C can select the image capture sequence on the display 206 positioned at the first end 214 of the housing 212 that faces the clinician C.

Figure 5:
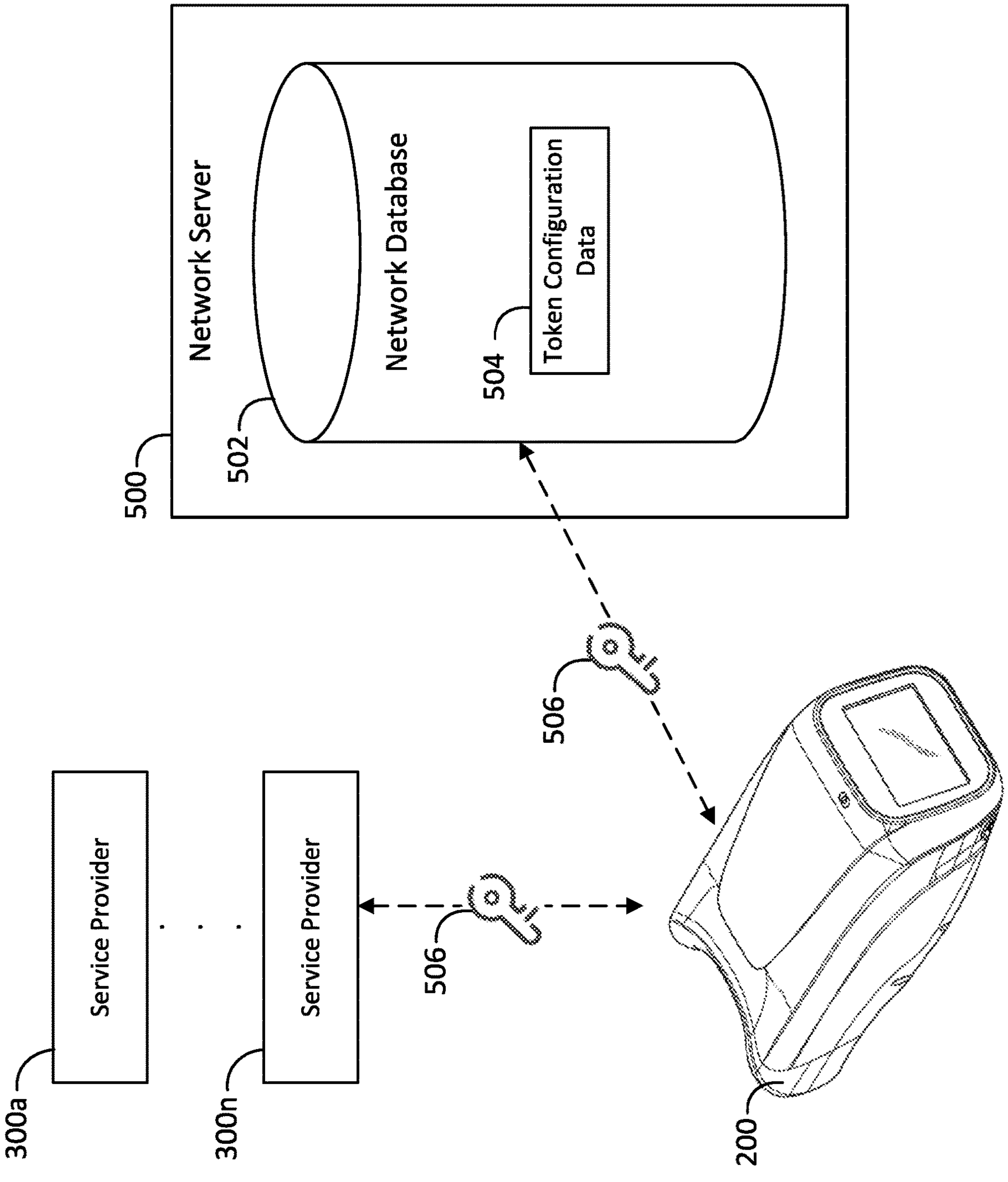
FIG. 5 schematically illustrates an example of a token transfer between the medical device and network server of FIG. 1, and one or more external service providers.

FIG. 5 schematically illustrates an example of a token transfer between the network server 500 and the medical device 200, and the one or more external service providers 300*a*-300*n*. In some examples, at least some of the one or more external service providers 300*a*-300*n* belong to a separate third-party system distinct from the medical device 200 and the network server 500. Also, at least some of the one or more external service providers 300*a*-300*n* can provide overread services for analyzing diagnostic data captured by the medical device 200. In some further examples, at least some of the one or more external service providers 300*a*-300*n* include proprietary systems that belong to a common owner/manufacturer of at least one of the medical device 200 and the network server 500. In some further examples, at least some of the one or more external service providers 300*a*-300*n* include an electronic medical record (EMR) system. The token transfer between the medical device 200, the network server 500, and the one or more external service providers 300*a*-300*n* can be performed over the network 102.

The network server 500 generates tokens 506 for authentication of the medical device 200 to utilize the services of the one or more external service providers 300*a*-300*n*. The tokens 506 generated by the network server 500 establish a trust relationship between the medical device 200 and the one or more external service providers 300*a*-300*n*, allowing the medical device 200 to access the operations and/or data of the external service providers 300*a*-300*n*.

The network server 500 customizes the tokens 506 such that the tokens 506 are unique for each of the one or more external service providers 300*a*-300*n*. As an illustrative example, the network server 500 generates a first type of customized token for the medical device 200 to access a first external service provider, a second type of customized token for the medical device 200 to access a second external service provider, a third type of customized token for the medical device 200 to access a third external service provider, and so on.

Also, while a single medical device is shown in FIG. 5, the system 100 can include a plurality of medical devices. The network server 500 customizes the tokens that are generated for each medical device in the system 100 such that the customized tokens are unique per medical device in addition to being unique for each of the external service providers.

The tokens 506 are generated by the network server 500 using token configuration data 504 stored within the network database 502. As noted above, the tokens 506 are customized and unique for each of the external service providers such that the token configuration data 504 includes the specifications and/or requirements requested by each external service provider 300.

Figure 6:
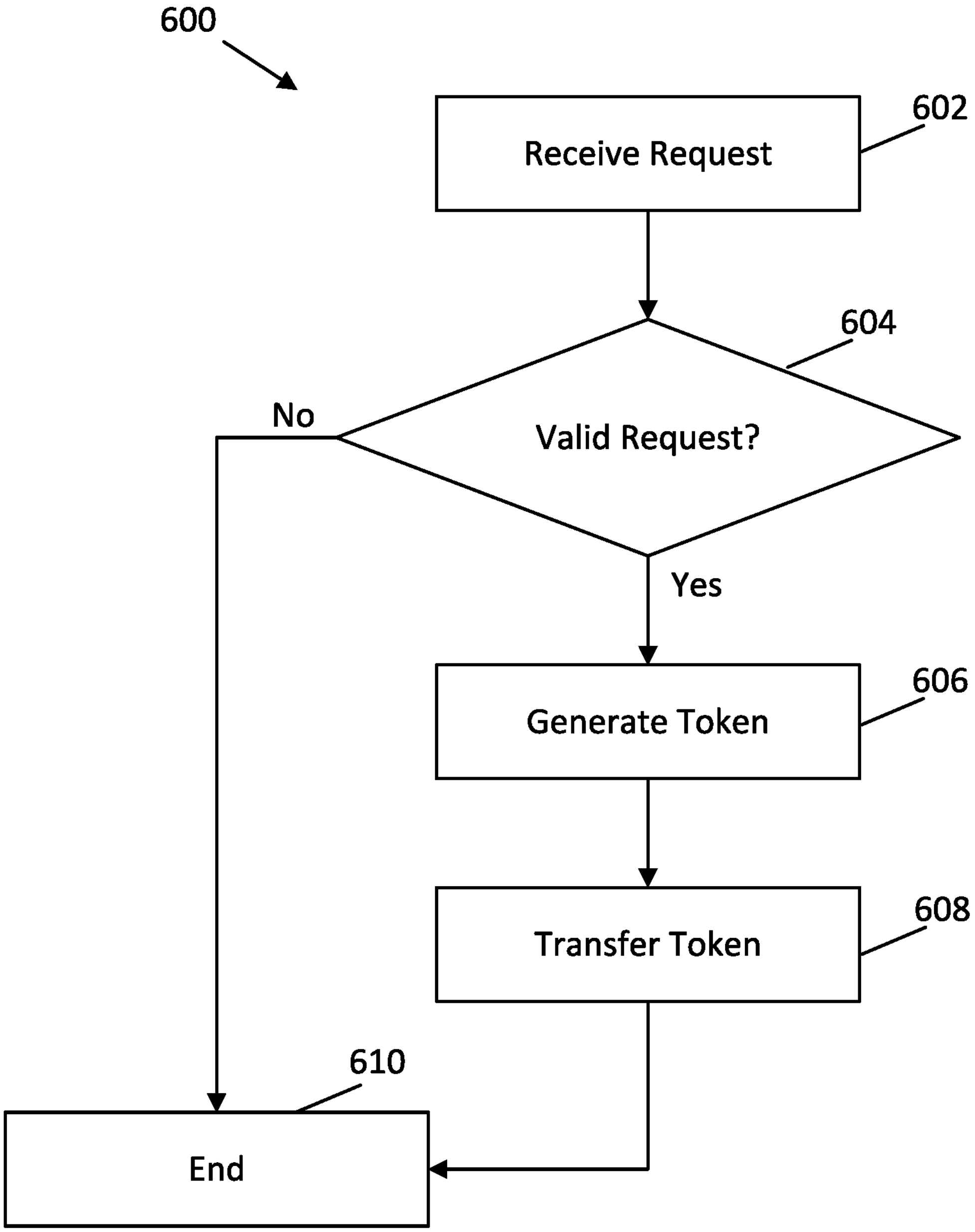
FIG. 6 schematically illustrates an example of a method of authenticating the medical device of FIG. 1 to one or more external service providers.

FIG. 6 schematically illustrates an example of a method 600 of authenticating the medical device 200 to the one or more external service providers 300*a*-300*n*. In some instances, the method 600 can be performed by the network server 500.

As shown in FIG. 6, the method 600 includes an operation 602 of receiving a request from the medical device 200 to access the operations and/or data of an external service provider 300. In some examples, the request is received by the network server 500 when the clinician selects a workflow on the medical device 200, such as by using the display 206. The request can include information that identifies the medical device 200 such as a device serial number.

Next, the method 600 includes an operation 604 of determining whether the request received from the medical device 200 is valid. Operation 604 can include using the information in the request to validate the medical device 200. As an illustrative example, operation 604 can include comparing the serial number of the medical device 200 to a list of trusted devices to confirm the validity of the request. Also, operation 604 can include determining whether the medical device 200 is authorized to access the operations and/or data of an external service provider 300 by checking a service type or subscription activated on the medical device.

Examples of the workflows that can be executed on the medical device 200 based on a service type assigned and/or activated on the medical device 200 can include guiding a user to operate the medical device 200 to capture an image showing a region of interest, to align an optical axis of the medical device 200 with the region of interest, to guide the user through an eye fundus image capturing process, to execute an automated script for capture of the eye fundus image, to allow for manual capture of the eye fundus image, to automatically move a camera until a bright spot associated with a reflection of a cornea of the eye is positioned for automatic capture of the image of the eye, to automate a quality assessment of a digital eye fundus image, to estimate one or more disease states, to provide a workflow based on a risk score for a given patient, to perform a microvascular assessment based on captured eye images, to calculate one or more vital signs based on an eye fundus video, and the like.

When the request is determined not to be valid (i.e., "No" in operation 604), the method 600 terminates at operation 610. When the request is determined to be valid (i.e., "Yes" in operation 604), the method 600 proceeds to an operation 606 of generating the token. Operation 606 includes generating a unique token specific to the external service provider 300 identified in the request received in operation 602 such that the token cannot be used by the medical device 200 to access the operations and/or data of a different external service provider 300.

The method 600 includes an operation 608 of transferring the token to the medical device 200. Thereafter, the medical device 200 can use the token to access the operations and/or data of the external service provider 300 identified in the request received in operation 602. The token includes an expiration time (e.g., 10-25 minutes) such that the token cannot be used by the medical device 200 to access the external service provider 300 beyond a certain time limit. Also, in some examples, the token is not reusable such that the token expires after it has been used by the medical device 200 to access the operations and/or data of the external service provider 300.

Figure 7:
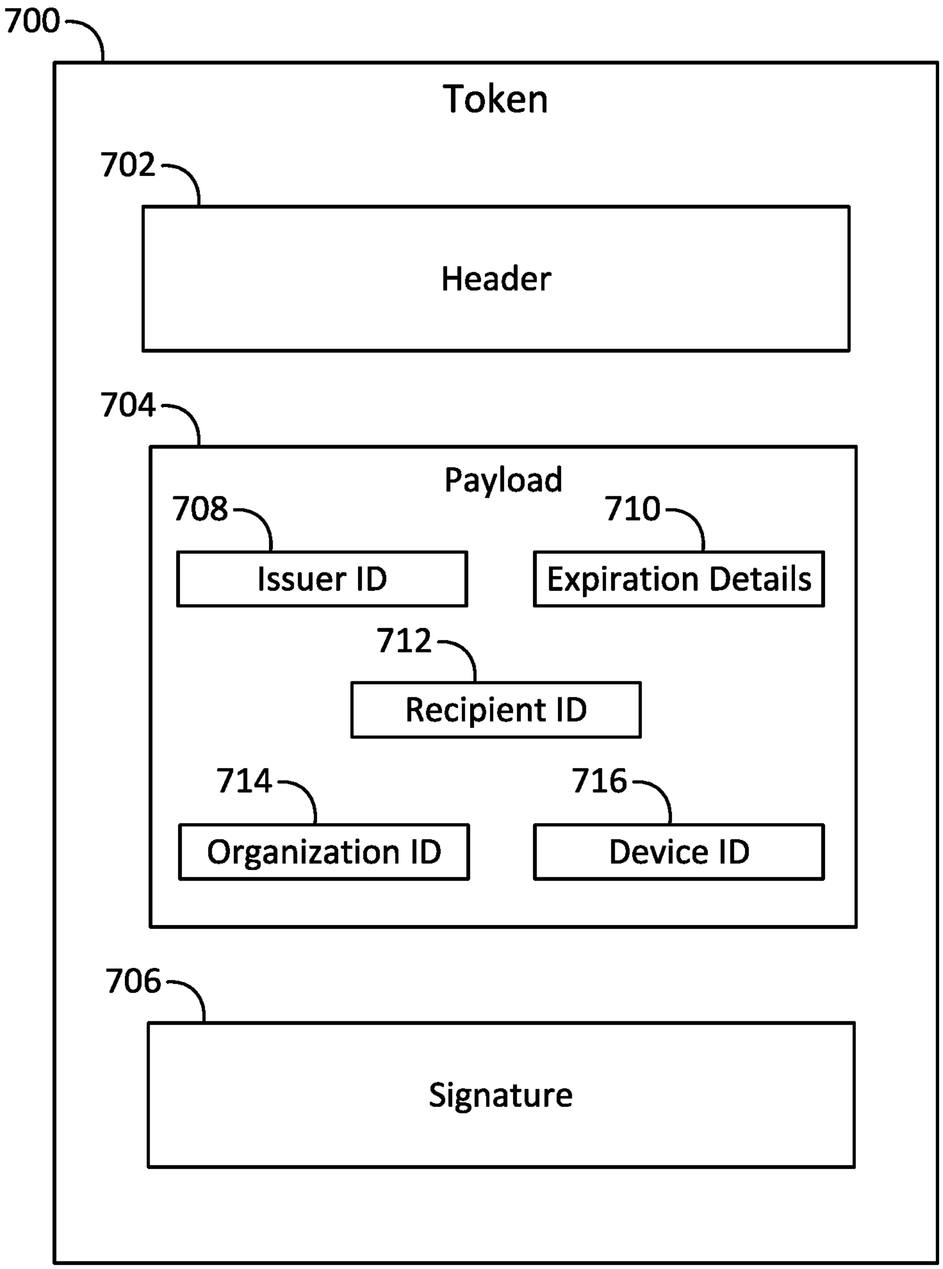
FIG. 7 schematically illustrates an example of a token generated by the network server of FIG. 1.

FIG. 7 schematically illustrates an example of a token 700 generated by the network server 500 in accordance with the examples described above. The token 700 can be used by the medical device to access the operations and/or data of an external service provider 300.

As shown in FIG. 7, the token 700 includes a header 702, a payload 704, and a signature 706. The header 702 includes a token type parameter, and an algorithm parameter. The token type parameter is a static value that identifies the standard used to create the token (e.g., JSON Web Token (JWT)). The algorithm parameter identifies the cryptographic algorithm used to sign and/or encrypt the token 700. In some examples, the header 702 follows a standardized format based on one or more standards such as JSON Web Signature (JWS), JSON Web Token (JWT), Open Authorization (OAuth), OpenID Connect (OIDC), or other type of standard.

In the example shown in FIG. 7, the payload 704 includes a first data set 708 identifying the issuer of the token 700 (e.g., network server 500), a second data set 710 identifying the expiration details of the token 700 (e.g., start and expiration times of the token, such that when current time is before the start time or after the expiration time, the token is considered invalid), a third data set 712 identifying the audience(s) or intended recipient(s) of the token 700 (e.g., an external service provider 300), a fourth data set 714 identifying an organization such as an owner and/or customer of the medical device 200, and a fifth data set 716 identifying the medical device 200 (e.g., device serial number). The payload 704 can include additional data or less data depending on the specifications and/or requirements requested by an external service provider 300. As noted above, the token 700 is customized and unique for each of the external service providers such that the payload 704 can be customized based on the specifications and/or requirements requested by each external service provider 300.

The signature 706 is used to verify that the sender of the token 700 (e.g., the network server 500) is who it says it is and to ensure that the message contained in the token 700 was not changed along the way. To create the signature, the header 702 and the payload 704 are encoded and signed with the algorithm specified in the header 702.

Figure 8:
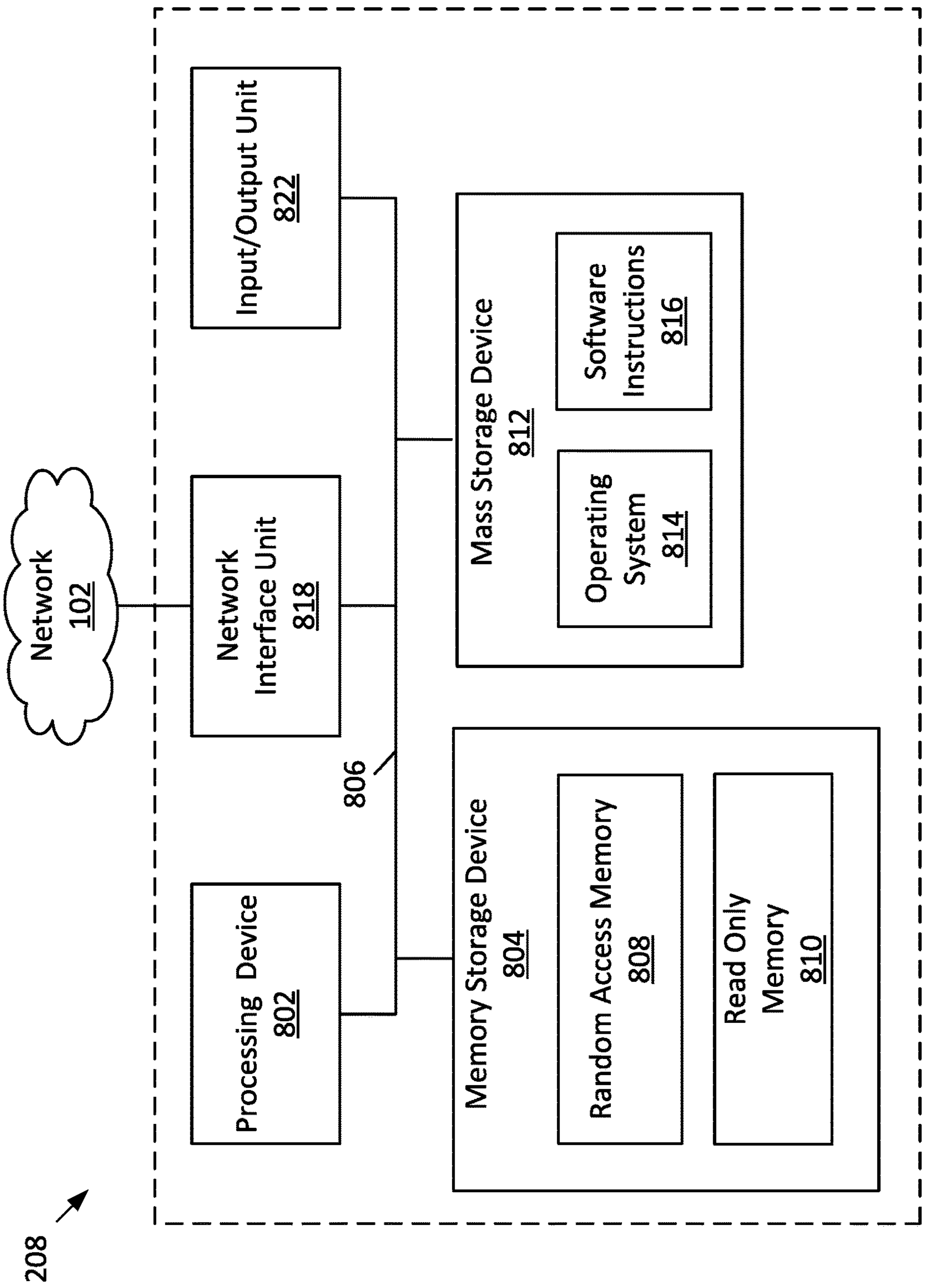
FIG. 8 schematically illustrates an example of a computing device that can be used to implement aspects of the system of FIG. 1.

FIG. 8 schematically illustrates an example of the computing device 208 that can be used to implement aspects of the system 100 such as the medical device 200, the one or more external service providers 300*a*-300*n*, and/or the network server 500. The computing device 208 includes one or more processing devices 802, a memory storage device 804, and a system bus 806 that couples the memory storage device 804 to the one or more processing devices 802. The one or more processing devices 802 can include central processing units (CPU).

As shown in FIG. 8, the memory storage device 804 can include a random-access memory ("RAM") 808 and a read-only memory ("ROM") 810. Basic input and output logic having basic routines that help to transfer information between elements within the computing device 208, such as during startup, can be stored in the ROM 810.

The computing device 208 can further include a mass storage device 812 that can include an operating system 814, and store software instructions 816. The mass storage device 812 is connected to the one or more processing devices 802 through the system bus 806. The mass storage device 812 and associated computer-readable data storage media provide non-volatile, non-transitory storage for the computing device 208.

Although the description of computer-readable data storage media contained herein refers to the mass storage device 812, it should be appreciated by those skilled in the art that computer-readable data storage media can be any available non-transitory, physical device or article of manufacture from which the computing device 208 can read data and/or instructions. The computer-readable storage media can be comprised of entirely non-transitory media. The mass storage device 812 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, or any other medium which can be used to store information, and which can be accessed by the device.

The computing device 208 operates in a networked environment using logical connections to the other devices through the network 102. The computing device 208 connects to the network 102 through a network interface unit 818 connected to the system bus 806. The network interface unit 818 can also connect to additional types of communications networks and devices, including Bluetooth, Wi-Fi, and cellular telecommunications networks including 4G and 5G networks. The network interface unit 818 can connect the computing device 208 to additional networks, systems, and devices. The computing device 208 further includes an input/output unit 822 for receiving and processing inputs and outputs. In examples where the display 206 is a touchscreen, the display 206 is both an input and output device.

The mass storage device 812 and the RAM 808 can store software instructions and data. The software instructions can include an operating system 814 for operating the computing device 208. The mass storage device 812 and/or the RAM 808 can also store software instructions 816, which when executed by the processing device 802, provide the various functions and aspects of the computing device 208 discussed herein.

The various embodiments described above are provided by way of illustration only and should not be construed to be limiting in any way. Various modifications can be made to the embodiments described above without departing from the true spirit and scope of the disclosure.

What is claimed is:

1. A system for authenticating a medical device, the system comprising: at least one processing device; a network database storing token configuration data comprising specifications requested by a plurality of external service providers, wherein the network database is separate from and independent of the plurality of external service providers; and a memory device storing instructions which, when executed by the at least one processing device, cause the at least one processing device to: receive a request from the medical device to access operations or data of an external service provider, wherein the external service provider is configured for analyzing diagnostic data captured by the medical device; determine whether the request received from the medical device is valid; when the request is valid, access the token configuration data stored in the network database to retrieve the specifications requested by the external service provider identified in the request; generate a token on behalf of the medical device, the token having a payload that is customized based on the specifications requested by the external service provider identified in the request, wherein the specifications requested by the external service provider include content specifications for the payload such that tokens generated for different external service providers have different payload structures, wherein the payload is customized to include data identifying an issuer of the token, an expiration of the token, a recipient of the token, an organization to which the medical device belongs, and data identifying the medical device; and transfer the token to the medical device, the token enabling the medical device to access the operations or data of the external service provider.

2. The system of claim 1, wherein the instructions, when executed by the at least one processing device, further cause the at least one processing device to:

receive a second request from the medical device to access operations or data of a second external service provider;

determine whether the second request received from the medical device is valid;

when the second request is valid, generate a second token that is customized based on the second external service provider identified in the second request; and transfer the second token to the medical device, the second token enabling the medical device to access the operations or data of the second external service provider, wherein the second token includes a payload having a different data set than the payload of the first token.

3. The system of claim 1, wherein the diagnostic data includes eye fundus images.

4. The system of claim 1, wherein the instructions, when executed by the at least one processing device, further cause the at least one processing device to:

determine whether the medical device is authorized to access the operations or data of the external service provider by checking a service type activated on the medical device.

5. The system of claim 1, wherein the instructions, when executed by the at least one processing device, further cause the at least one processing device to:

generate a plurality of tokens;

transfer the plurality of tokens to the medical device, the plurality of tokens enabling the medical device to access operations or data of a plurality of external service providers, wherein each token of the plurality of tokens is unique for each external service provider of the plurality of external service providers.

6. The system of claim 5, further comprising:

a plurality of medical devices; and wherein the instructions, when executed by the at least one processing device, further cause the at least one processing device to:

generate the plurality of tokens for each medical device of the plurality of medical devices such that each token of the plurality of tokens is unique per medical device in addition to being unique for each external service provider of the plurality of external service providers.

7. A method for authenticating a medical device, the method comprising: receiving a request from the medical device to access operations or data of an external service provider, wherein the external service provider is configured for analyzing diagnostic data captured by the medical device; determining whether the request received from the medical device is valid; when the request is valid, accessing token configuration data stored in a network database to retrieve specifications requested by the external service provider identified in the request; generating a token on behalf of the medical device, the token having a payload that is customized based on the specifications requested by the external service provider identified in the request, wherein the specifications requested by the external service provider include content specifications for the payload such that tokens generated for different external service providers have different payload structures, wherein the payload is customized to include data identifying an issuer of the token, an expiration of the token, a recipient of the token, an organization to which the medical device belongs, and data identifying the medical device; and transferring the token to the medical device, the token enabling the medical device to access the operations or data of the external service provider.

8. The method of claim 7, further comprising:

receiving a second request from the medical device to access operations or data of a second external service provider;

determining whether the second request received from the medical device is valid;

when the second request is valid, generating a second token that is customized based on the second external service provider identified in the second request; and transferring the second token to the medical device, the second token enabling the medical device to access the operations or data of the second external service provider, wherein the second token includes a payload having a different data set than the payload of the first token.

9. The method of claim 7, wherein the diagnostic data includes eye fundus images.

10. A non-transitory computer-readable data storage medium comprising instructions that, when executed, cause at least one computing device to: receive a request from a medical device to access operations or data of an external service provider, wherein the external service provider is configured for analyzing diagnostic data captured by the medical device; determine whether the request received from the medical device is valid; when the request is valid, access token configuration data stored in a network database to retrieve specifications requested by the external service provider identified in the request; generate a token on behalf of the medical device, the token having a payload that is customized based on the specifications requested by the external service provider identified in the request, wherein the specifications requested by the external service provider include content specifications for the payload such that tokens generated for different external service providers have different payload structures, wherein the payload is customized to include data identifying an issuer of the token, an expiration of the token, a recipient of the token, an organization to which the medical device belongs, and data identifying the medical device; and transfer the token to the medical device, the token enabling the medical device to access the operations or data of the external service provider.

11. The non-transitory computer-readable data storage medium of claim 10, wherein the instructions, when executed, further cause the at least one computing device to:

receive a second request from the medical device to access operations or data of a second external service provider;

determine whether the second request received from the medical device is valid;

when the second request is valid, generate a second token that is customized based on the second external service provider identified in the second request; and transfer the second token to the medical device, the second token enabling the medical device to access the operations or data of the second external service provider, wherein the second token includes a payload having a different data set than the payload of the first token.

12. The non-transitory computer-readable data storage medium of claim 10, wherein the diagnostic data includes eye fundus images.

* * * * *